United States Patent
Noda et al.

(10) Patent No.: US 6,903,053 B2
(45) Date of Patent: Jun. 7, 2005

(54) AGRICULTURAL ITEMS AND AGRICULTURAL METHODS COMPRISING BIODEGRADABLE COPOLYMERS

(75) Inventors: Isao Noda, Fairfield, OH (US); Michael Matthew Satkowski, Oxford, OH (US)

(73) Assignee: The Procter & Gamble Company, Cincinnati, OH (US)

(*) Notice: Subject to any disclaimer, the term of this patent is extended or adjusted under 35 U.S.C. 154(b) by 0 days.

(21) Appl. No.: 10/309,997

(22) Filed: Dec. 4, 2002

(65) Prior Publication Data

US 2003/0145518 A1 Aug. 7, 2003

Related U.S. Application Data

(63) Continuation of application No. PCT/US01/18748, filed on Jun. 8, 2001.
(60) Provisional application No. 60/210,557, filed on Jun. 9, 2000.

(51) Int. Cl.[7] .............................. A01N 25/10; C05G 5/00
(52) U.S. Cl. ....................... 504/360; 514/950; 514/953; 71/64.13
(58) Field of Search ........................ 504/360; 514/950, 514/953; 71/64.13

(56) References Cited

U.S. PATENT DOCUMENTS

| | | |
|---|---|---|
| 3,932,319 A | 1/1976 | Clendinning et al. |
| 4,686,790 A | 8/1987 | Lahalih et al. |
| 5,165,351 A | 11/1992 | Billings |
| 5,207,020 A | 5/1993 | Aslam et al. |
| 5,292,860 A | 3/1994 | Shiotani et al. |
| 5,498,692 A | 3/1996 | Noda |
| 5,502,116 A | 3/1996 | Noda |
| 5,503,883 A | 4/1996 | Kell, Jr. et al. |
| 5,536,564 A | 7/1996 | Noda |
| 5,602,227 A | 2/1997 | Noda |
| 5,618,855 A | 4/1997 | Noda |
| 5,685,756 A | 11/1997 | Noda |
| 5,747,584 A | 5/1998 | Noda |
| 5,760,118 A | 6/1998 | Sinclair et al. |
| 5,837,029 A | 11/1998 | Behel, Jr. et al. |
| 5,837,273 A | 11/1998 | Shasha et al. |
| 5,883,104 A | 3/1999 | Wood et al. |
| 5,885,604 A | 3/1999 | Ballinger, Jr. |
| 5,914,295 A | 6/1999 | Hoffmann et al. |
| RE36,548 E | 2/2000 | Noda |
| 6,071,998 A | 6/2000 | Muller et al. |
| 6,077,931 A | 6/2000 | Noda |
| 6,160,199 A | 12/2000 | Noda |
| 6,174,990 B1 | 1/2001 | Noda |
| 6,214,920 B1 | 4/2001 | Muller et al. |
| 6,410,096 B1 | 6/2002 | Eggink et al. |

FOREIGN PATENT DOCUMENTS

| | | |
|---|---|---|
| EP | 0 843 963 B1 | 12/2002 |
| JP | 05-085902 A | 4/1993 |
| JP | 05-163110 A | 6/1993 |
| JP | 07-324227 A | 12/1995 |
| WO | WO 92/18553 A1 | 10/1992 |
| WO | WO 95/20614 A1 | 8/1995 |
| WO | WO 95/20615 A1 | 8/1995 |
| WO | WO 99/04948 A1 | 2/1999 |
| WO | WO 01/30892 A1 | 5/2001 |
| WO | WO 01/30893 A1 | 5/2001 |

OTHER PUBLICATIONS

Schimtz, Peter, et al., "Films", Ullmann's Encyclopedia of Industrial Chemistry, 5th Ed., vol. A11, 1988, pp. 85–95, 108–110.

*Primary Examiner*—S. Mark Clardy
(74) *Attorney, Agent, or Firm*—Julie A. McConihay; Angela Marie Stone; Leonard W. Lewis

(57) ABSTRACT

An agricultural item comprising a biodegradable polyhydroxyalkanoate copolymer comprising two randomly repeating monomer units. The first randomly repeating monomer unit has the structure:

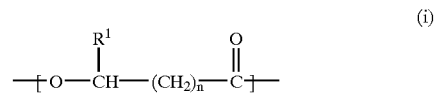

(i)

wherein $R^1$ is H or a $C_{1-2}$ alkyl, and n is 1 or 2; and the second randomly repeating monomer unit has the structure:

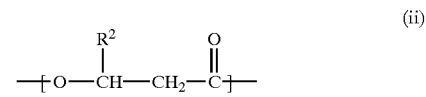

(ii)

wherein $R^2$ is a $C_{3-19}$ alkyl or a $C_{3-19}$ alkenyl. At least 50% of the randomly repeating monomer units have the structure of the first randomly repeating monomer unit.

20 Claims, No Drawings

AGRICULTURAL ITEMS AND AGRICULTURAL METHODS COMPRISING BIODEGRADABLE COPOLYMERS

CROSS REFERENCE TO RELATED APPLICATION

This application is a continuation of International Application PCT/US01/18748, with an international filing date of Jun. 8, 2001, and published in English, which claims the benefit of U.S. Provisional Application No. 60/210,557, filed Jun. 9, 2000.

TECHNICAL FIELD

This invention relates to agricultural items and agricultural methods. More particularly, the invention relates to agricultural items comprising biodegradable polyhydroxyalkanoates, methods of treating a plant comprising contacting at least a portion of a plant with a composition comprising biodegradable polyhydroxyalkanoates, and a method for the controlled release of chemicals comprising treating chemicals with biodegradable polyhydroxyalkanoates.

BACKGROUND ART

Polymers find uses in a variety of plastic articles including films, sheets, fibers, foams, molded articles, adhesives and many other specialty products. The majority of this plastic material ends up in the solid waste stream. While some efforts at recycling have been made, repeated processing of even pure polymers results in degradation of material and consequently poor mechanical properties. Different grades of chemically similar plastics mixed upon collection can cause processing problems that make the reclaimed material inferior or unusable.

Agricultural items such as erosion control covers, mulches, nets, twines, pots and plant stakes may be formed from plastics. It would be advantageous for such items to be biodegradable. For example, agricultural mulches are used to retard weed growth, increase moisture retention by the soil, and prevent erosion. However, if the mulches are not degradable, the mulch must be removed from the field at the end of each season. It would be efficient to use a mulch which is biodegradable, and did not require removal at the end of the growing season.

Clendinning et al., U.S. Pat. No. 3,932,319, disclose films and containers, which may be used as transplanter containers, fabricated from material comprising a biodegradable thermoplastic dialkanoyl polymer. Clendinning et al. teach that containers may be formed from a blend of the biodegradable thermoplastic dialkanoyl polymer and a naturally occurring biodegradable product such as soya bean meal, peat moss, corn starch, wood chips, flours and starches.

Lahalih et al., U.S. Pat. No. 4,686,790, disclose agricultural mulch films prepared by mixing conventional plant nutrients with a water-soluble polymer, such as polyvinyl alcohol, to form a thin film. Lahalih et al. further teach the dry film is then coated with a thin layer of water-resistant resin, such as polyvinyl acetate, to form a composite mulch film.

Billings, U.S. Pat. No. 5,165,351, discloses a seed planter unit which utilizes a biodegradable seed tape. Billings further teaches that fertilizer and agricultural chemicals may be incorporated into the seed tape or into a separately dispensed tape for controlled application of the chemicals adjacent to the crops.

Aslam et al., U.S. Pat. No. 5,207,020, disclose an erosion control blanket made of recycled, biodegradable, split and expanded sheets of paper. Aslam et al. teach the blanket has a plurality of layers such as the upper layers promote run-off to reduce erosion, while lower layers trap water which passes through the blanket passing the water to the soil and trapping loose soil particles.

Kell, Jr. et al., U.S. Pat. No. 5,503,883, disclose a biodegradable wreath ring comprising a ring constructed from multiple layers of paper strips laminated one over another in the radial direction of the ring and bonded with a biodegradable resin or adhesive.

Sinclair et al., U.S. Pat. No. 5,760,118, disclose that hydrolytically degradable polymers may be used in the production of products for the controlled release of chemicals, such as biocides, fertilizers, attractants to attract pests into traps, repellants, mildewcides, fungicides, and fertilizers. Sinclair et al. further disclose the hydrolytically degradable polymers may be used for garden products such as root ball covers, geo-textile erosion control, weed control film, mulch, seed mats, seed strips, pots, stakes and twines, as well as items such as toys, clothes, absorbent items and containers.

Behel, Jr. et al., U.S. Pat. No. 5,837,029, teach the inclusion of organic hydroxy acids and iron sulfate formulations in hydrophilic polymer delivery systems. Behel, Jr. et al. teach a delivery system forms particles which can be metered into soil in or near a plant row.

Shasha et al., U.S. Pat. No. 5,837,273, teach compositions for encapsulating biologically active material into starch-based adherent granules. Shasha et al. teach such granules are capable of sustained release of pest control agents.

Wood et al., U.S. Pat. No. 5,883,104, disclose methods of improving the residual control of mites and prolonging the protection of plants from mite infestations by applying to plant foliage an unsymmetrical 4,6-bis(aryloxy)pyrimidine compound.

Ballinger, Jr., U.S. Pat. No. 5,885,604, discloses methods for deterring birds from damaging planted seeds by applying to the seeds before planting or to the surface of the ground overlaying the planted seeds a non-toxic solid coating material which is repellant to the taste to birds and absorbs light at a wave length in the range of 300 to 400 mm.

Kim et al., EP 0843963A1, disclose a pesticide formulation comprising pesticide and biodegradable thermoplastic polyester resin. Kim et al. teach the formulation provides for controlled release of the active ingredient.

Asrar et al., WO 99/04948, disclose methods of producing coated objects comprising melting a polyhydroxyalkanote, such as polyhydroxybutyrate or polyhydroxy-butyrate-co-valerate, and extrusion coating the object. Asrar et al. teach the coating has a molecular weight of greater than 125,000 daltons.

Thus, there is continuing need in the agricultural field for items formed from biodegradable plastics. Preferably the plastics would have great flexibility and strength without excessive thickness. Further, it is desirable that such biodegradable plastics be substantially free of or free of plasticizers which may leak from the plastic articles. There is a further need for methods of delaying or controlling the release of agricultural chemicals.

Unfortunately, many biodegradable items are brittle, or are incapable of degrading under both aerobic and anaerobic conditions. Further, prior art polymers such as polyhydroxybutyrate and poly(hydroxybutyrate-co-hydroxyvalerate)

often have unsatisfactory properties. Polyhydroxybutyrate and poly(hydroxybutyrate-co-hydroxyvalerate) tend to become thermally unstable near their melt temperatures, which make processing difficult. It is preferred that the melting temperature of a biodegradable material be substantially lower than its decomposition temperature.

SUMMARY OF THE INVENTION

Accordingly, it is an object of this invention to obviate various problems of the prior art.

It is another object of this invention to provide agricultural items which are biodegradable.

It is another object of this invention to provide agricultural items which can degrade under both aerobic and anaerobic conditions.

It is yet another object of this invention to provide methods of treating plants comprising contacting at least a portion of a plant with a composition comprising a biodegradable polymer.

Additionally, it is an object of this invention to provide methods for the controlled release of chemicals, preferably agricultural chemicals such as fertilizers, pesticides, herbicides, fungicides, compounds that are unpalatable to animals and compounds which are attractants to beneficial insects.

It is another object of this invention to provide for ground covers, mulches and erosion control films which are flexible and strong, and which may be transparent or opaque.

It is also an object of this invention to provide for a method of reducing moisture loss through plant leaves and petals.

It is another object of this invention to provide delivery vehicles for agricultural compounds which provide time controlled release of the chemical, which are easy to handle, and which promote worker safety by containing the active compounds during application.

In accordance with one aspect of the invention there is provided agricultural items comprising a biodegradable polyhydroxyalkanoate copolymer comprising two randomly repeating monomer units wherein the first randomly repeating monomer unit has the structure:

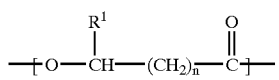

(i)

wherein $R^1$ is H or a $C_{1-2}$ alkyl, and n is 1 or 2; and
the second randomly repeating monomer unit has the structure:

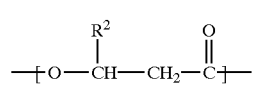

(ii)

wherein $R^2$ is a $C_{3-19}$ alkyl or a $C_{3-19}$ alkenyl; and
wherein at least 50% of the randomly repeating monomer units have the structure of the first randomly repeating monomer unit.

In accordance with another aspect of the invention there is provide methods of treating a plant comprising the step of contacting at least a portion of a plant with a composition comprising a biodegradable polyhydroxyalkanoate copolymer comprising two randomly repeating monomer units wherein the first randomly repeating monomer unit has the structure:

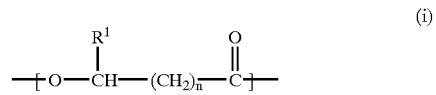

(i)

wherein $R^1$ is H or a $C_{1-2}$ alkyl, and n is 1 or 2; and
the second randomly repeating monomer unit has the structure:

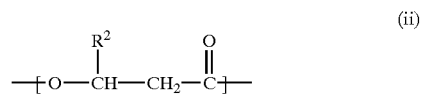

(ii)

wherein $R^2$ is a $C_{3-19}$ alkyl or a $C_{3-19}$ alkenyl; and
wherein at least 50% of the randomly repeating monomer units have the structure of the first randomly repeating monomer unit.

Additionally, methods for the controlled release of a chemical are provided. The methods comprise treating the chemical with a biodegradable polyhydroxyalkanoate copolymer comprising two randomly repeating monomer units wherein the first randomly repeating monomer unit has the structure:

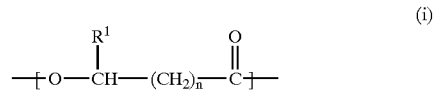

(i)

wherein $R^1$ is H or a $C_{1-2}$ alkyl, and n is 1 or 2; and
the second randomly repeating monomer unit has the structure:

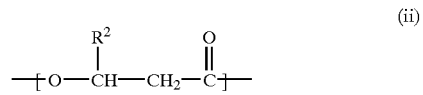

(ii)

wherein $R^2$ is a $C_{3-19}$ alkyl or a $C_{3-19}$ alkenyl; and
wherein at least 50% of the randomly repeating monomer units have the structure of the first randomly repeating monomer unit.

DETAILED DESCRIPTION

Applicants have found that compositions comprising polyhydroxyalkanoate polymers (PHAs) provide useful agricultural items. Polyhydroxyalkanoates polymers are a particularly useful vehicle for delaying and controlling the release of chemicals. PHAs in accordance with the present invention will biodegrade under both aerobic and anaerobic conditions, thus, items formed from the PHAs can biodegrade even when under water.

Biodegradable items in accordance with the invention are unexpectedly resistant to liquids and grease. The items are formed from PHAs having softening temperatures greater than their intended storage and use temperatures and are therefore suitable for being stored in warehouses during summer without losing dimensional stability. The items are formed from PHAs which exhibit surprisingly good self-sealability and adhesion to paper substrates.

Further, unlike the homopolymer poly(3-hydroxybutyrate) (PHB) or the copoymer poly(3- hydroxybutryate-co-3-hydroxyvalerate) (PHBV), PHAs in accordance with the invention are tough without being brittle. Thus items comprising the PHAs are less likely to crack or chip. Applicants have found that polyhydroxyalkanoates in accordance with the present invention have lower melt temperatures, lower degrees of crystallinity and improved melt rheologies relative to polyhydroxybutyrate and polyhydroxy-butyrate-co-valerate. As the PHAs of the present invention have low melting temperatures, the PHAs are easily processed into films and coatings. The PHAs of the present invention have melting temperatures lower than their decomposition temperatures.

As used herein, "agricultural items" is intended to include any items used in agriculture other than untreated soil, untreated plants, and untreated portions of plants such as seed, stems, flowers, and fruit. Agricultural items include erosion control covers, ground covers, root ball covers, nets, pots, vases, wreath rings, mulches, plant stakes, fencing stakes, labels, twines, ropes and foliage sprays. Agricultural items also include coated or encapsulated plants, portions of plants or chemicals, such as a polymer coated seeds and/or chemicals, biodegradable tapes or mats comprising seeds and/or chemicals, and granules, tablets or pellets for the controlled release of chemicals. As used herein, "agricultural chemicals" is intended to include chemicals used in agriculture, such as fertilizers, pesticides, herbicides, fungicides, mildewcides, compounds that are unpalatable to animals and compounds which are attractants to beneficial insects. Agricultural chemicals include urea, nitrates, phosphates, potassium, magnesium and iron sulfate.

As used herein, "alkyl" refers to a saturated carbon-containing chain which may be straight or branched, and substituted (mono- or poly-) or unsubstituted, while, "alkenyl" refers to a carbon-containing chain which may be mono-unsaturated (i.e., one double bond in the chain) or poly-unsaturated (i.e., two or mor double bonds in the chain), straight or branched, and substituted (mono- or poly-) or unsubstituted.

As used herein, "PHA" refers to a polyhydroxyalkanoate of the present invention; "PHB" refers to the homopolymer poly(3-hydroxybutyrate); and "PHBV" refers to the copolymer poly(3-hydroxybutyrate-co-3-hydroxyvalerate).

As used herein, "biodegradable" refers to the ability of a compound to ultimately be degraded completely into $CH_4$, $CO_2$, and water or biomass by microorganisms and/or natural environmental factors.

As used herein, "compostable" refers to a material that meets the following three requirements: (1) the material is capable of being processed in a composting facility for solid waste; (2) if so processed, the material will end up in the final compost; and (3) if the compost is used in the soil, the material will ultimately biodegrade in the soil.

For example, a polymer film material present in solid waste submitted to a composting facility for processing does not necessarily end up in the final compost. Certain composting facilities subject the solid waste stream to air classification prior to further processing, in order to separate paper and other materials. A polymer film would most probably be separated from the solid waste stream in such an air classification and therefore not be processed in the composting facility. Nevertheless, it may still be a "compostable" material according to the above definition because it is "capable" of being processed in a composting facility.

The requirement that the material ends up in the final compost typically means that it undergoes a form of degradation in the composting process. Typically, the solid waste stream will be subjected to a shredding step in an early phase of the composting process. As a result, the polymer film will be present as shreds rather than a sheet. In the final phase of the composting process, the finished compost will be subjected to a screening step. Typically, the polymer shreds will not pass through the screens if they have retained the size they had immediately after the shredding step. The compostable materials of the present invention will have lost enough of their integrity during the composting process to allow partially degraded shreds to pass through the screens. However, it is conceivable that a composting facility might subject the solid waste stream to a very rigorous shredding and a rather coarse screening, in which case nondegradable polymers like polyethylene would meet requirement (2). Therefore, meeting requirement (2) is not enough for a material to be compostable within the present definition.

What distinguishes the compostable material as defined herein from material like polyethylene is requirement (3), that the material ultimately biodegrade in the soil. This biodegradability requirement is not essential to the composting process or the use of composting soil. Solid waste and the compost resulting therefrom may contain all kinds of nonbiodegradable materials, for example, sand. However, to avoid a build up of man-made materials in the soil, it is required herein that such materials be fully biodegradable. By the same token, it is not at all necessary that this biodegradation be fast. As long as the material itself and intermediate decomposition products are not toxic or otherwise harmful to the soil or crops, it is fully acceptable that their biodegradation takes several months or even years, since this requirement is present only to avoid an accumulation of man-made material in the soil. The copolymers according to the invention advantageously undergo rapid anaerobic biodegradation.

All copolymer composition ratios recited herein refer to molar ratios, unless specifically indicated otherwise. All parts and percentages are by weight, unless specifically indicated otherwise.

The polyhydroxyalkanoates used in the present invention made be synthetically prepared, or may be produced by a variety of biological organisms, such as bacteria or algae. The polyhydroxyalkanoate may be a homopolymer or a copolymer, preferably the polyhydroxyalkanoate is a copolymer.

The polyhydroxyalkanoates may be atactic, isotactic or syndiotactic. The polyhydroxyalkanoates used herein are preferably substantially isotactic (from about 90% to about 100%, by weight, isotactic) or fully isotactic (about 100%, by weight, isotactic). The fully isotactic polyhydroxyalkanoates may be obtained from biological organisms, preferably polyhydroxyalkanoates used herein are obtained from biological organisms.

The polyhydroxyalkanoates are copolymers comprising at least about 2 different monomers. In some embodiment, the polyhydroxyalkanoates are copolymers comprising at least about 3 different monomers.

In one embodiment, the polyhydroxyalkanoate comprises at least two randomly repeating monomer units (RRMUs). The first randomly repeating monomer unit has the structure:

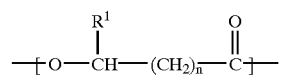

wherein $R^1$ is H or a $C_{1-2}$ alkyl, and n is 1 or 2. In a preferred embodiment, the first randomly repeating monomer unit is selected from the group consisting of the monomer wherein $R^1$ is a $C_1$ alkyl and n is 1 (the monomeric repeat unit 3-hydroxybutyrate); the monomer wherein $R^1$ is a $C_2$ alkyl and n is 1 (the monomeric repeat unit 3-hydroxyvalerate); the monomer wherein $R^1$ is H and n is 2 (the monomeric repeat unit 4-hydroxybutyrate); the monomer wherein $R^1$ is H and n is 1 (the monomeric repeat unit 3-hydroxypropionate); and mixtures thereof.

The second randomly repeating monomer unit has the structure:

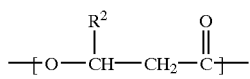

wherein $R^2$ is a $C_{3-19}$ alkyl or a $C_{3-19}$ alkenyl. Suitable second RRMUs include those wherein $R^2$ is a $C_{3-7}$ alkyl or alkenyl, a $C_5$ alkyl or alkenyl, a $C_7$ alkyl or alkenyl, a $C_{8-11}$ alkyl or alkenyl, a $C_8$ alkyl or alkenyl, a $C_9$ alkyl or alkenyl, a $C_{12-19}$ alkyl or alkenyl, a $C_{3-11}$ alkyl or alkenyl, or a $C_{4-19}$ alkyl or alkenyl.

In one embodiment of the present invention, at least about 50%, preferably at least about 60%, more preferably at least about 70%, even more preferably at least about 80%, more preferably still at least about 85%, of the RRMUs have the structure of the first RRMU.

When the polyhydroxyalkanoates of the present invention are processed into films, sheets, or soft elastic fibers, preferably from about 50% to about 98%, more preferably from about 80% to about 97%, even more preferably from about 85% to about 96%, of the RRMUs of the PHAs have the structure of the first RRMU.

When the polyhydroxyalkanoates of the present invention are processed into normal fibers or molded articles (e.g., injected or blow molded), preferably from about 80% to about 99%, more preferably from about 90% to about 98%, even more preferably from about 95% to about 97%, of the RRMUs of the PHAs have the structure of the first RRMU.

When the polyhydroxyalkanoates of the present invention are processed into thermoformed articles, preferably from about 70% to about 98%, more preferably from about 75% to about 97%, even more preferably from about 80% to about 96%, of the blend RRMUs of the PHAs have the structure of the first RRMU.

When the polyhydroxyalkanoates of the present invention are processed into foam, preferably from about 70% to about 97%, more preferably from about −80% to about 96%, even more preferably from about 86% to about 95%, of the blend RRMUs of the PHAs have the structure of the first RRMU.

When the polyhydroxyalkanoates of the present invention are processed into elastomers or adhesives, preferably about 50%, more preferably at least 65%, of the RRMUs of the PHAs have the structure of the first RRMU.

When the polyhydroxyalkanoates of the present invention are processed into nonwoven fabrics, preferably from about 85% to about 99%, more preferably from about 90% to about 98%, even more preferably from about 95% to about 97%, of the RRMUs of the PHAs have the structure of the first RRMU.

When the polyhydroxyalkanoates of the present invention are processed into molded articles, e.g., injection or blow molded, preferably from about 80% to about 90%, more preferably from about 90% to about 98%, even more preferably from about 92% to about 97%, of the RRMUs of the PHAs have the structure of the first RRMU.

In a preferred embodiment, the first randomly repeating monomer unit is selected from the group consisting of the monomer wherein $R^1$ is a $C_1$ alkyl and n is 1 (the monomeric repeat unit 3-hydroxybutyrate); the monomer wherein $R^1$ is a $C_2$ alkyl and n is 1 (the monomeric repeat unit 3-hydroxyvalerate); the monomer wherein $R^1$ is H and n is 2 (the monomeric repeat unit 4-hydroxybutyrate); the monomer wherein $R^1$ is H and n is 1 (the monomeric repeat unit 3-hydroxypropionate) and mixtures thereof.

In another embodiment, the copolymer useful in the present invention comprises a third or more additional RRMUs having the structure:

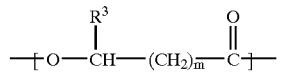

wherein $R^3$ is H, a $C_{1-19}$ alkyl or a $C_{1-19}$ alkenyl, and m is 1 or 2; and wherein the additional RRMUs are not the same as the first RRMU or the second RRMU. The copolymer may comprise from at least about 3, more preferably from about 3 to about 20 different RRMUs.

In one embodiment, $R^3$ is a $C_{1-19}$ alkyl or a $C_{1-19}$ alkenyl, and m is 1, while in another embodiment $R^3$ is a H, a $C_{1-2}$ alkyl or a $C_{1-2}$ alkenyl, and m is 1 or 2. In a preferred embodiment, the third RRMU is selected from the group consisting of the monomer wherein $R^3$ is a $C_1$ alkyl and m is 1 (the monomeric repeat unit 3-hydroxybutyrate); the monomer wherein $R^3$ is a $C_2$ alkyl and m is 1 (the monomeric repeat unit 3-hydroxyvalerate); the monomer wherein $R^3$ is H and m is 2, (the monomeric repeat unit 4-hydroxybutyrate); the monomer wherein $R^3$ is H and m is 1, (the monomeric repeat unit 3-hydroxypropionate) and mixtures thereof.

In one embodiment the PHA of the present invention comprises two RRMUs wherein the first RRMU has the structure:

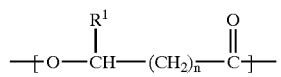

wherein $R^1$ is H or a $C_2$ alkyl, and n is 1 or 2; and the second RRMU has the structure:

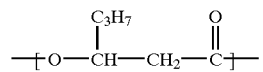

Preferably at least 50% of the RRMUs have the structure of the first RRMU.

The one embodiment the biodegradable PHA of the present invention comprises three RRMUs, a first RRMU having the structure:

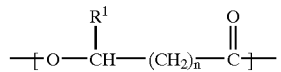

wherein $R^1$ is H or a $C_{1-2}$ alkyl, and n is 1 or 2; a second RRMU having the structure:

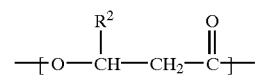

wherein $R^2$ is a $C_{3-19}$ alkyl or a $C_{3-19}$ alkenyl, preferably a $C_{4-19}$ alkyl or a $C_{4-19}$ alkenyl; and a third RRMU having the structure:

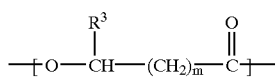

wherein a $R^3$ is H, a $C_{1-19}$ alkyl or a $C_{1-19}$ alkenyl, and m is 1 or 2; and wherein the third RRMU is not the same as the first RRMU or the second RRMU. Preferably at least 50% of the RRMUs have the structure of the first RRMU. Generally no more than about 20% of the RRMUs have the structure of the third RRMU.

Preferably the molecular weight of the polyhydroxyalkanoate is greater than about 50,000. In one embodiment the weight average molecular weight is no greater than about 400,000. In another embodiment the weight average molecular weight is greater than about 400,000, preferably greater than 500,000.

The volume percent crystallinity ($\Phi_c$) of a semi-crystalline polymer (or copolymer) often determines what type of end-use properties the polymer possesses. For example, highly (greater than 50%) crystalline polymers are generally strong and stiff, and suitable for products such as stakes and pots. Low crystalline polymers are generally flexible and tough, and suitable for products such as ground covers. Crystallinity can be determined in a number of ways, including x-ray diffraction, differential scanning calorimetry (DSC), density measurements, and infrared absorption, as discussed by Noda, U.S. Pat. No. 5,618,855, incorporated herein by reference.

In general, PHAs of the present invention preferably have a crystallinity of from about 50% to about 95% as measured via x-ray diffraction; more preferably from about 10% to about 80%; more preferably still from about 20% to about 60%.

When a PHA of the present invention is to be processed into a film, the amount of crystallinity in such PHA is more preferably from about 5% to about 60% as measured via x-ray diffraction; more preferably from about 10% to about 50%; more preferably still from about 20% to about 40%.

When a PHA of the present invention is to be processed into a sheet, the amount of crystallinity in such PHA is more preferably from about 5% to about 60% as measured via x-ray diffraction; more preferably from about 10% to about 50%; more preferably still from about 20% to about 40%.

When a PHA of the present invention is to be processed into a normal fiber or a nonwoven fabric, the amount of crystallinity in such PHA is more preferably from about 50% to about 95% as measured via x-ray diffraction; more preferably from about 60% to about 95%; more preferably still from about 70% to about 95%.

When a PHA of the present invention is to be processed into a soft elastic fiber, the amount of crystallinity in such PHA is more preferably from about 20% to about 90% as measured via x-ray diffraction; more preferably from about 30% to about 85%; more preferably still from about 40% to about 80%.

When a PHA of the present invention is to be processed into a molded or thermoformed article, the amount of crystallinity in such PHA is more preferably from about 10% to about 80% as measured via x-ray diffraction; more preferably from about 20% to about 70%; more preferably still from about 30% to about 60%.

When a PHA of the present invention is to be processed into an elastomer or adhesive, the amount of crystallinity in such PHA is more preferably less than about 50% as measured via x-ray diffraction; more preferably less than about 30%; more preferably still less than about 20%.

Preferably, the biodegradable PHAs of the present invention have a melt temperature (Tm) of from about 30° C. to about 160° C., more preferably from about 60° C. to about 140° C., more preferably still from about 90° C. to about 130° C.

Suitable polyhydroxyalkanoates include those disclosed in Noda, U.S. Pat. Nos. 5,498,692; 5,502,116; 5,536,564; 5,602,227; 5,618,855; 5,685,756; and 5,747,584, incorporated herein by reference.

Many plastic items comprise plasticizers such as phthalate plasticizers or adipic acid derivatives such as di-2-ethylhexyladipate. Phthalate plasticizers refer to compounds comprising a phthalate group used as plasticizers. Such plasticizers include bis-2-ethylhexyl phthalate, also referred to as dioctyl phthalate (DOP) and di-2-ethylhexyl phthalate (DEHP), and diisononyl phthalate (DINP). Other phthalate plasticizers include butyl benzyl phthalate, butyl octyl phthalate, di-n-butyl phthalate, dicapryl phthalate, dicyclohexyl phthalate, diethyl phthalate, dihexyl phthalate, diisobutyl phthalate, diisodecyl phthalate, diisohectyl phthalate, diisooctyl phthalate, dimethyl phthalate, ditridecyl phthalate, diundecyl phthalate, undecyl dodecyl phthalate and mixtures thereof.

However, there is concern that plasticizers, particularly phthalate plasticizers, may leach from plastic items. Thus, the present agricultural items are preferably substantially free of, more preferably free of, plasticizers, particularly phthalate plasticizers. As used herein, substantially free of means preferably no greater than 20%, more preferably no greater than 10%, even more preferably less than 5%, by weight, of the item is plasticizers. In one embodiment the item is free of plasticizers.

In another emodiment, the agricultural items may contain plasticizers, preferably non-toxic and biodegradable plasticizers. Suitable plasticizers include tricarboxylic esters, citrate esters, esters of glycerine and dicarboxylic esters. A preferred plasticizer is triacetin, also called glyceryl triacetate or 1,2,3-propanetriol triacetate. Generally, agricultural items containing plasticizers comprises from no greater than 20%, preferably no greater than 10%, even more preferably less than 5%, by weight of total PHA items.

The agricultural items may contain additives such as agricultural chemicals, colorants or antibacterial compounds. Preferably the additives are nonfugitive. As used herein, "nonfugitive" refers to an additive that does not escape from the polyhydroxyalkanoate copolymer at a faster rate than which the copolymer biodegrades.

The items used herein may be in the form of films, sheets, fibers, foams, thermoformed items and molded articles. As used herein, "film" means an extremely thin continuous piece of a substance having a high length to thickness ratio and a high width to thickness ratio. While there is no requirement for a precise upper limit of thickness, a preferred upper limit is about 0.25 mm, more preferably about 0.10 mm, and even more preferably about 0.05 mm. The films may be processed using conventional procedures for producing single or multilayer films on conventional film-making equipment.

As used herein, "sheet" means a very thin continuous piece of a substance, having a high length to thickness ratio and a high width to thickness ratio, wherein the material is thicker than about 0.25 mm. Sheeting shares many of the same characteristics as film in terms of properties and manufacture, with the exception that sheeting is stiffer, and has a self-supporting nature.

As used herein, "fiber" refers to a flexible, macroscopically homogeneous body having a high length-to-width ratio and a small cross section. As used herein, "foam" refers to copolymers of the present invention whose apparent density has been substantially decreased by the presence of numerous cells distributed throughout its bulk. In another embodiment of the present invention, the plastic article is a molded article. As used herein, "molded articles" refers to objects that are formed from compositions which are injected, compressed, or blown by means of a gas into a shape defined by a mold. As used here, "thermoformed articles" refers objects formed by heating planks or sheets of the polyhydroxyalkanoate until flexible and then stamping or vacuum pulling the planks or sheets into the proper shape.

In one embodiment, biodegradable polyhydroxyalkanoate copolymers are used to produce agricultural items such as erosion control covers, ground covers, root ball covers, nets, pots, vases, wreath rings, mulches, plant stakes, fencing stakes, labels, twines and ropes. Agricultural items also include coated or encapsulated plants, portions of plants or chemicals, such as a polymer coated seeds and/or chemicals, biodegradable tapes or mats comprises seeds and/or chemicals, and granules, tablets or pellets for the controlled release of chemicals. Items such as wreath rings, stakes, and pots may be molded thermoformed or foam articles, while articles such as tarps, nets, ground covers and mulches may be sheets or films and articles such as nets, twines and ropes may be fibers.

In a preferred embodiment, the polyhydroxyalkanoate copolymer is in the form of a film. The film may be used as a mulch, or a protective cover. Such a film is biodegradable, has good flexibility and strength, and, if desired, may be made transparent, opaque, or colored. The polyhydroxyalkanoate copolymer protective covers, such as wraps, tarps, nets or films, may be placed over plants, including trees, perennials, annual plants and crops. Such biodegradable protective covers would protect plants from pests such as locusts, beetles, and birds.

A film in the form of a mulch would decrease weed growth while increasing moisture retention. Mulches may be in the form of solid films, films having slits or holes, or shredded films. Biodegradable mulches and protective films would, in addition to promoting good plants growth, provide savings and time and money because such biodegradable items would not require removal or disposal. The films or mulches could simply be plowed into the soil after the growing season is over.

In a more preferred embodiment, the mulch further comprises an agricultural chemical, such as a fertilizer, pesticide, herbicide, fungicide, mildewcide, a compound which is unpalatable to animals which may destroy the plants, or a compound which is attractive to beneficial insects. Suitable agricultural chemicals include urea, nitrates, phosphate, potassium, magnesium and iron sulfate. As the mulch slowly biodegrades, the agricultural chemical would be slowly released.

In one embodiment, the copolymer forms a seed tape or seed mat. That is, a tape or mat comprising the polyhydroxyalkanoate copolymer further comprises seeds. The tape or mat is placed in or on the ground, and the copolymer serves as a support for the seed. In one embodiment, the seed tape or seed mat further comprises an agricultural chemical.

Mulches and seed tapes or mats comprising agricultural chemicals are ways in which the polyhydroxyalkanoate copolymers may serve as a delivery vehicle for agricultural use. Such a delivery system may allow for the controlled release of seeds and/or chemicals, and may take any other convenient form. For example, the delivery system can be in the form of strips, stakes, tablets, granules, erosion control covers, nets, pots, sheetings and microcapsules. Such delivery devises offer numerous advantages. In addition to controlling the release of the agricultural chemical over time and controlling the location of the release, such delivery vehicles contain odors of the active ingredient. Further, such delivery systems provide for worker safety; as the active compound is contained within the delivery device during application the worker experiences less exposure to the active compound.

In another embodiment, two separate tapes or mats are applied to the ground, one tape or mat comprising the polyhydroxyalkanoate copolymer and seeds, the other tape or mat comprising the polyhydroxyalkanoate copolymer and at least one agricultural chemical. As the copolymer biodegrades, it releases the agricultural product. Thus, there can be a controlled release of the agricultural product over time. Further, the agricultural chemical can be directed for specific areas. For example, rather than widely dispersing a chemical such as a fertilizer or pesticide over an entire field or garden, tapes or mats containing the chemical can be placed close to the plants, thereby localizing the chemical near the plant.

Chemicals may be encapsulated by the polyhydroxyalkanoate, thereby forming capsules, granules, or tablets. Alternatively, an item comprising the polyhydroxyalkanoate may have the agricultural chemical dispersed throughout the item.

The delivery vehicle may comprise two different portions which may be designed for a different rates of degradation. For example, a tape may have a thin layer comprising seeds, which quickly degrades and releases the seeds, and at least one thicker layer comprising chemicals which are more slowly released over time. Similarly, a mulch or erosion ground cover may comprise layers which degrade at different rates, thereby releasing chemicals at different times or at different rates. In another embodiment a granular composition comprises chemicals having biodegradable coatings of different thickness, for example, a composition may comprise at least two types of different granules, wherein one type of granule has a thicker polymeric coating than the other. The chemicals which are thinly coated will be released more quickly than chemicals which are thickly coated.

Compositions comprising polyhydroxyalkanoate copolymers may be used in methods of treating plants. The method of treating plants comprise the step of contacting at least a portion of a plant with a composition comprising the biodegradable polyhydroxyalkanoate copolymer.

The plants may be sprayed, painted or otherwise contacted with a composition containing polymer particles dispersed in a carrier; the composition may further comprise an agricultural chemical. The plant portions which may be contacted with the composition includes roots, leaves, fruits, buds, stems, twigs, branches, flowers and seeds.

For example, the polyalkanoate copolymer may be used in a plant protector to spray on leaves, stems and twigs. Such coating would decrease the amount of moisture loss through the plants without interfering with plant growth, respiration, osmosis or photosynthesis. In one embodiment the composition is used to coat fruit while it is growing, thereby protecting the fruit from excessive moisture loss. The composition would be easily applied, and as the composition is biodegradable, there would be no need for removal. Further, the composition may comprise agricultural chemicals such as pesticides, herbicides, fungicides and mildewcides to further protect the plant from adverse conditions.

Cut flowers may be dipped or sprayed with the composition to decrease moisture loss through the flowers in order to keep the flowers looking fresh longer. The composition may be used to change the appearance of a plant by giving the plant a shiny or flocked appearance. For example, Christmas trees or wreathes may be sprayed with a biodegradable composition comprising polyalkanoate which gives the appearance of flocking or "artificial snow." Additionally, the composition would slow moisture loss from the Christmas trees or wreathes.

Coating or encapsulating seeds would protect the seeds during storage from dehydration. Further, the composition may additionally comprise agricultural chemicals which would protect the seeds from plants pathogens such as fungi, mildews, viruses and bacteria. Alternatively, the composition may comprise fertilizer to promote plant growth during early stages, or may comprise an ingredient which is unpalatable to animals so that animals do not consume the seeds during storage or germination. As used herein "compounds unpalatable to animals" include compounds which are unpalatable to mammals, reptiles, amphibians, insects, arachnids and birds.

In another embodiment a method of treating plants and/or soil comprises spraying a composition comprising a polyhydroxyalkanoate copolymer and an agricultural chemical onto the surface of soil either before or after planting. The controlled release of the agricultural chemical into the soil surrounding the plants places portions of the plants, particularly seeds, roots and stems, in contact with the agricultural chemical. Such a method may be particularly useful as a treatment method for root vegetables such as carrots, potatoes and turnips. An agriculturally acceptable soil pH may be maintained by the slow release of a pH adjusting chemical, such as lime, from a composition comprising a polyhydroxyalkanoate copolymer and the pH adjusting agent.

Preferred agricultural items are formed from a polyhydroxyalkanoate comprising two randomly repeating monomer units. The first randomly repeating monomer unit has the structure:

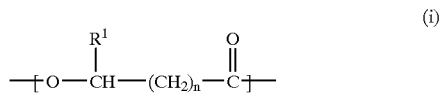

(i)

wherein $R^1$ is H or a $C_{1-2}$ alkyl, and n is 1 or 2; and the second randomly repeating monomer unit has the structure:

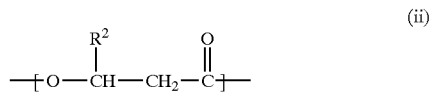

(ii)

wherein $R^2$ is a $C_{3-19}$ alkyl or a $C_{3-19}$ alkenyl, preferably a $C_{4-19}$ alkyl or a $C_{4-19}$ alkenyl. In another embodiment the polyhydroxyalkanoate comprises a third randomly repeating monomer unit having the structure:

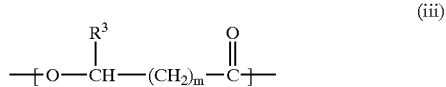

(iii)

wherein $R^3$ is H, a $C_{1-19}$ alkyl or a $C_{1-19}$ alkenyl, and m is 1 or 2, and the third RRMU is not the same as the first RRMU or the second RRMU. Polyhydroxyalkanoate copolymers comprising three RRMUs will generally comprise, by weight, at least about 50% of the first RRMU, and generally no greater than about 20% of the third RRMU. The composition may comprise at least about 4%, more preferably at least about 5%, and even more preferably at least about 8%, and no more than about 15%, preferably no more than about 12%, more preferably no more than about 10%, by weight, of the third RRMU. The preferred levels of monomers is dependent upon the desired characteristic of the article, that is, whether the article is a foam article, a molded article, a thermoformed article, an extruded article, or whether the article comprises a wood or paper substrate having a copolymer coating.

In one embodiment, agricultural items such as mulches and ground covers are films or sheets comprising a PHA. Preferably the films or sheets comprising a PHA which comprises a first RRMU having formula (i) above, and a second RRMU having formula (ii) above. Preferably from about 50% to about 98%, more preferably from about 80% to about 97%, even more preferably from about 85% to about 90%, of the RRMUs of the PHA have the structure of the first RRMU. The weight average molecular weight of the PHA is greater than about 400,000. In one embodiment the films or sheets comprise no more than 20%, by weight of total PHA, of the third RRMU having the formula (iii) above.

In one embodiment, agricultural items such as pots, vases and stakes are molded articles comprising a PHA. The PHA preferably comprises a first RRMU having formula (i) above, and a second RRMU having formula (ii) above. Preferably from about 80% to about 99%, more preferably from about 90% to about 98%, even more preferably from about 92% to about 97%, of the blend RRMUs of the PHA have the structure of the first RRMU. The weight average molecular weight of the copolymer is no greater than about 500,000. In one embodiment the food service items are molded articles comprising no greater than about 20%, preferably less than about 15%, by weight of total PHA, of the third RRMU having the formula (iii) above.

In another embodiment, agricultural items such as pots, vases and stakes are thermoformed articles comprising a PHA. The PHA preferably comprises a first RRMU having formula (i) above, and a second RRMU having formula (ii) above. Preferably from about 70% to about 98%, more preferably from about 75% to about 97%, even more preferably from about 80% to about 96%, of the blend RRMUs of the PHA have the structure of the first RRMU. The weight average molecular weight of the copolymer is no greater than about 500,000, preferably less than about 400,000. In one embodiment the thermoformed articles comprise from about 3% to about 15%, by weight of total PHA, of the third RRMU having the formula (iii) above.

In yet another embodiment, items such as pots, vases, wreath rings and stakes are formed from a PHA foam. The PHA preferably comprises a first RRMU having formula (i) above, and a second RRMU having formula (ii) above. Generally the PHA has a weight average molecular weight of no greater than 500,000, preferably less than about 400,000. In one embodiment the PHA foam comprises no greater than about 70% preferably less than about 15% by weight of total PHA, of the third RRMU having the formula (iii) above.

In one embodiment, items such as strings and stakes are extruded items comprising a PHA. The PHA preferably comprises a first RRMU having formula (i) above, and a second RRMU having formula (ii) above. Preferably the weight average of molecular weight of the copolymer is greater than 400,000. In one embodiment the extruded items comprise from about 6% to about 15%, by weight of total PHA, of the third RRMU having the formula (iii) above.

In one embodiment, the agricultural items such as transplanting pots and stakes comprise a substrate having a coating comprising a PHA. Coating wooden substrates, such as wooden stakes, with a coating comprising PHA provides the wooden substrate with a smoother surface than that of untreated wood.

The PHAs used as coatings preferably comprise a first RRMU having formula (i) above, and a second RRMU having formula (ii) above. Preferably the weight average molecular weight of the copolymer is greater than 100,000, preferably greater than about 200,000. In one embodiment the PHAs used as coatings comprise no greater than about 20%, preferably less than about 15%, by weight of total PHA, of the third RRMU having the formula (iii) above. The coatings may further comprise colorants in order to provide the items with a more attractive appearance. The coatings may be applied to pre-formed articles in any convenient manner, such as spraying, dipping or extrusion coating.

In one embodiment, films or sheets comprising a PHA are used to laminate substrates such as stakes. Preferably the films or sheets comprise a PHA which comprises a first RRMU having formula (i) above, and a second RRMU having formula (ii) above. Preferably from about 50% to about 99%, more preferably from about 80% to about 98%, even more preferably from about 90% to about 97%, of the RRMUs of the PHA have the structure of the first RRMU. The weight average molecular weight of the PHA is generally greater than 100,000, preferably greater than 200,000. In one embodiment the films or sheets comprise no greater than bout 20%, preferably less than about 15%, by weight of total PHA, of the third RRMU having the formula (iii) above.

In another embodiment the agricultural item is a compositions for treating plaints or soil comprising a PHA and a carrier, and, optionally an agricultural chemical. The carrier is a compound which will not damage the plant. In one embodiment the carrier will evaporate after treatment of the plant or soil, thereby leaving behind a thin layer of PHA. Suitable carriers include water, alcohols, ketons and esters. Preferably the PHA which comprises a first RRMU having formula (i) above, and a second RRMU having formula (ii) above. Preferably from about 50% to about 99%, more preferably from about 70% to about 90%, of the RRMUs of the PHA have the structure of the first RRMU. The weight average molecular weight of the PHA is no greater than 500,000. In one embodiment the compositions comprise no greater than about 20%, preferably less than about 15%, by weight of total PHA, of the third RRMU having the formula (iii) above.

"Articles comprising PHAs may be made by any art-recognized process, such as those disclosed in Noda, U.S. Pat. Nos. 5,618,855 and 5,602,227, incorporated herein by reference. For example, mulches and ground covers may be in the form of films or sheets. Films may be processed using conventional procedures for producing single or multilayer films on conventional film-making equipment. Pellets of the PHAs of the present invention can be first dry blended and then melt mixed in a film extrude. Alternatively, if insufficient mixing occurs in the film extruder, the pellets can be first dry blended and then melt mixed in a precompounding extruder followed by repelletization prior to film extrusion."

The PHAs of the present invention can be melt processed into films using either cast or blown film extrusion methods. Cast film is extruded through a linear slot die. Generally the flat web is cooled on a large moving polished metal roll. It quickly cools, and peels off this first roll, passes over one or more auxiliary cooling rolls, then through a set of rubber-coated pull or "haul-off" rolls, and finally to a winder.

In blown film extrusion, the melt is extruded upward through a thin annular die opening. This process is also referred to as tubular film extrusion. Air is introduced through the center of the die to inflate the tube and thereby causing it to expand. A moving bubble is thus formed which is held at a constant size by control of internal air pressure. The tube of film is cooled by air, blown through one or more chill rings surrounding the tube. The tube is then collapsed by drawing it into a flattening frame through a pair of pull rolls and into a winder. The flattened tubular film is subsequently slit open, unfolded, and further slit into widths appropriate for use in products.

Both cast film and blown film processes can be used to produce either monolayer or multilayer film structures. For the production of monolayer films from a single thermoplastic material or blend of thermoplastic components only a single extruder and single manifold die are required. For the production of multilayer films of the present invention, co-extrusion processes are preferably employed. Such processes require more than one extruder and either a co-extrusion feedblock or multi-manifold die system or combination of the two to achieve the multilayer film structure.

Sheets may be formed by cast extrusion, rolling or calendering. Rolling produces a film with predominately machine direction orientation by accelerating the film from a nip point where the thickness is reduced. Large forces are found at the nip point, but overall orientation can be increased over other forms of machine direction orientation.

Calendering may be used to produce an unoriented cast film or sheet with high throughput, calendering is used. The calendering process employs stacks of specially hardened, driven rolls, supported in a manner so they may be bent or skewed in position relative to each other during operation. This is to control thickness in the calendered material. Calenders are usually made up of four rolls that form three nips. These nips are the feed, metering and finishing nips. The feed nip is where the polymer is supplied, mixed, and heated. The metering nip reduces the thickness of the sheet to the approximate final thickness. The finishing nip adjusts the gauge of the sheet by varying the position of the third or middle roll.

Nets, twines or ropes according to the present invention may be formed from fibers comprising PHAs. Fibers of the present invention may be processed using a variety of conventional techniques well-known in the art including, but not limited to, melt spinning, dry spinning and wet spinning. Combinations of these three basic processes are often used.

In melt spinning a PHA of the present invention is heated above its melting point and the molten PHA is forced through a spinneret. A spinneret is a die with many small orifices which are varied in number, shape and diameter. The jet of molten PHA is passed through a cooling zone where the PHA solidifies and is then transferred to post-drawing and take-up equipment.

In dry spinning a PHA of the present invention is dissolved and the PHA solution is extruded under pressure through a spinneret. The jet of PHA solution is passed through a heating zone where the solvent evaporates and the filament solidifies.

In wet spinning a PHA of the present invention is also dissolved and the solution is forced through a spinneret which is submerged in a coagulation bath. As the PHA solution emerges from the spinneret orifices within the coagulation bath, the PHA is either precipitated or chemically regenerated. Usually, all these processes need further drawing for useful properties to be obtained, for example to serve as textile fibers. "Drawing" refers to stretching and attenuation of fibers to achieve an irreversible extension, induce molecular orientation, and develop a fiber-fine structure). This fine structure is characterized by a high degree of crystallinity and by orientation of both the crystallites and the amorphous PHA chain segments.

Articles such as pots and stakes may be foam, thermoformed articles or molded articles. Foams are PHAs of the present invention whose apparent density has been substantially decreased by the presence of numerous cells distributed throughout its bulk. Foams of the present invention may be further categorized into flexible and rigid foams. This classification is based on a particular ASTM test procedure (see ASTM D, Vol. 37, pp. 1566–1578, American Society of Testing and Materials, Philadelphia, Polyaryl., (1978)). A flexible foam is a foam which does not rupture when a 20×2.5×2.5 cm piece is wrapped around a 2.5 cm mandrel at a uniform rate of 1 lap/5 s at 15°–25° C. Foams that do rupture under this test are referred to as rigid foams.

Foams of the present invention may be processed using conventional procedures well-known to those skilled in the art. A predominant method of foam production involves expanding a fluid polymer (or copolymer) phase to a low density cellular phase and then preserving this state. Other processes include leaching out materials that have been previously dispersed in the polymer (or copolymer), sintering small particles and dispersing cellular particles in a polymer (or copolymer). Three steps make up the expansion process. These are cell initiation, cell growth and cell stabilization. Many methods are used to create, grow, and stabilize cells.

Expandable formulations rely on increasing the pressure within the initiated cells relative to that of the surroundings. The cells are stabilized by either chemical (e.g. crosslinking, polymerization) or physical means (crystallization, melt-glass transition). A blowing agent such as isomeric pentanes and hexanes or halocarbons is mixed with the polymer (or copolymer) either by heating and allowing the blowing agent to penetrate the polymer, or by polymerizing the polymer in the presence of the blowing agent. Fabrication of articles is usually carried out in multiple steps, the first of which uses steam, hot water or hot air to expand the polymer into low density preformed beads. These preformed beads are aged, sometimes in multiple steps for correct cell size, and then packed into molds and fused together by heat and further expansion. Stabilization is accomplished by cooling the polymer to temperatures below its glass transition temperature.

Decompression expansion processes create and grow cells by lowering the external pressure during processing. Cellular polyethylene and polypropylene are often made in this manner. A decomposing blowing agent is premixed with the polymer (or copolymer) and fed through an extruder under elevated temperature and pressure such that the blowing agent partially decomposes. When the material exits the extruder, it enters a lower pressure zone. Simultaneous expansion and cooling take place, resulting in a stable cellular structure owing to rapid crystallization of the polymer.

Dispersion processes produce foams by directing dispersing solid or gas into the polymer (or copolymer) phase and then, when necessary, stabilizing the mixture. In one such process, frothing, a gas is mechanically dispersed in the polymer or monomer phase, producing a foam of temporary stability. This foam is then chemically stabilized by crosslinking or polymerization.

Molded articles can be solid objects or hollow. Injection molding of thermoplastics is a multi-step process by which a PHA of the present invention is heated until it is molten, then forced into a closed mold where it is shaped, and finally solidified by cooling. There are a variety of machines that are used in injection molding. Three common types are ram, screw plasticator with injection, and reciprocating screw devices. A ram injection molding machine is composed of a cylinder, spreader, and plunger. The plunger forces the melt in the mold. A screw plasticator with a second stage injection consists of a plasticator, directional valve, a cylinder without a spreader, and a ram. After plastication by the screw, the ram forces the melt into the mold. A reciprocating screw injection machine is composed of a barrel and a screw. The screw rotates to melt and mix the material and then moves forward to force the melt into the mold.

Compression molding in thermoplastics consists of charging a quantity of a PHA of the present invention in the lower half of an open die. The top and bottom halves of the die are brought together under pressure, and then molten PHA conforms to the shape of the die. The mold is then cooled to harden the plastic.

Blow molding is used for producing bottles and other hollow objects. In this process, a tube of molten PHA known as a parison is extruded into a closed, hollow mold. The parison is then expanded by a gas, thrusting the PHA against the walls of a mold. Subsequent cooling hardens the plastic. The mold is then opened and the article removed.

Blow molding has a number of advantages over injection molding. The pressures used are much lower than injection molding. Blow molding can be typically accomplished at pressures of from about 25 to about 100 psi between the plastic and the mold surface. By comparison, injection molding pressures can reach from about 10,000 to about 20,000 psi. In cases where the PHA has a have molecular weights too high for easy flow through molds, blow molding is the technique of choice. High molecular weight polymers (or copolymers) often have better properties than low molecular weight analogs, for example high molecular weight materials have greater resistance to environmental stress cracking. It is possible to make extremely thin walls in products with blow molding. This means less PHA is used, and solidification times are shorter, resulting in lower costs through material conservation and higher throughput. Another important feature of blow molding is that since it uses only a female mold, slight changes in extrusion conditions at the parison nozzle can vary wall thickness. This is an advantage with structures whose necessary wall thicknesses cannot be predicted in advance.

As used here, "thermoforming" refers to a process by which planks or sheets of the polyhydroxyalkanoate are heated until flexible and then stamped or vacuum pulled into the proper shape. Generally a sheet is fed through an oven and heated to bring it to a thermoformable temperature. The sheet is heated to a softening point and then advanced to a forming station. Alternatively, a sheet may move directly from an extruder to a forming station by means of a series of rolls, which can either be heated or cooled to bring the sheet to the proper thermoforming temperature. The forming station comprises molds or stamps of the desired shapes.

As used herein "nonwoven" means porous, textile like materials, usually in flat sheet form, composed primarily, or entirely, of fibers assembled in webs that are manufactured by processes other than spinning, weaving, or knitting. Other names for these materials are bonded fabrics, formed fabrics, or engineered fabrics. The thickness of the fabric sheets may vary from about 25 mm to several centimeters, and the weight from about 10 $g/m^2$ to about 1 $kg/m^2$. Nonwoven fabrics have a wide range of physical properties depending on the material and process used in forming the web. A fabric may be self-supporting and stiff as paper or drapable as a conventional cloth fabric.

In contrast to conventional textiles, the fundamental structure of all nonwovens is a web of fibers arranged more or less randomly. Thus, the key element is the single fiber. Tensile, tear, and tactile properties in the nonwoven arise from adhesive or other chemical and physical bonding, fiber-to-fiber friction created by entanglement, and reinforcement by other materials such as foams and films.

The nonwoven fabrics of the present invention may be made by conventional techniques known in the art. The production of nonwoven fabrics involves: 1) making fibers of various lengths and diameters; 2) creating a web of these fibers; and 3) bonding of fibers within the web by adhesive, or mechanical-frictional forces created by fiber contact or entanglement. In addition to these steps, reinforcing the web by forming a composite with other materials (e.g., yarns, scrims, films, nettings, and unbonded webs) is sometimes preferred. Variations of one or several of these steps allows for the enormous range of nonwoven fiber types. The term "staple fibers" was originally applied to fibers of natural origin long enough to be processed on textile machinery, but excluding endless filaments, e.g., silk. In the present context, as applied to PHA of the present invention, "staple fibers" are of relatively uniform length, from about 1.3 to about 10.2 cm, with a regular crimp i.e., a three-dimensional wavelike shape. Regenerated and other extruded fibers are endless as formed. They are cut during the manufacturing process to a specified length to meet a processing or market need. Extruded fibers are also produced as continuous filaments without crimp. The processes for forming webs from staple fibers are different from those using continuous filaments.

The choice of method for forming the web is determined by fiber length. Initially, the methods for forming webs from staple-length fibers (fibers long enough to be handled by conventional spinning equipment, usually from about 1.2 to about 20 cm long, but not endless) are based on the textile-carding process, whereas web formation from short fibers is based on papermaking technologies. Although these technologies are still in use, other methods have been subsequently developed. For example, webs are formed from long, virtually endless filaments directly from bulk polymer; both web and fibers are produced simultaneously. A variety of web-making methods are known, including carding, air-laying, wet-forming, spin-bonding, and melt-blowing.

The carding process is derived from the ancient manual methods of fiber carding, where natural staple fibers were manipulated by beds of needles. In carding, clumps of staple fibers are separated mechanically into individual fibers and formed into a coherent web by the mechanical action of moving beds of closely spaced needles.

In the air-laying process, the orientation created by carding is effectively improved by capturing fibers on a screen from an airstream. The fibers are separated by teeth or needles and introduced into an airstream. Total randomization would exclude any preferential orientation when the fibers are collected on the screen.

Wet-forming processes employ very short fibers. Initially, webs are formed from shod fibers by modified papermaking techniques. The fibers are continuously dispersed in a large volume of water and caught on a moving endless wire screen. Once the web is caught on the screen, it is transferred to belts or felts and dried on heated drums.

The spun-bonded web process involves making fibers and web simultaneously, directly from bulk polymer. The bulk polymer is melted, extruded, and drawn (often by triboelectric forces) to filaments that are randomized and deposited onto belts as a continuous web. The filaments are virtually endless. The spun-bond process produces webs of low crimp filaments in the normal diameter range of about 1.7 dtex (1.5 den) or slightly higher. The birefringence and uniformity of diameter of these filaments are similar to standard textile fibers and filaments.

Webs are also made directly from bulk polymers by the melt-blown process The molten PHA is forced through very fine holes in a special die into a high velocity airstream where the PHA is formed into very fine, although irregular, filaments of indeterminate lengths. The filaments are simultaneously formed into a web where melting and resolidification, and possibly static forces, hold them together. The web consists primarily of filaments with very fine diameters.

The bonding of fibers gives the strength to the web and influences other properties. Both adhesive and mechanical means are used. Mechanical bonding employs the engagement of fibers by frictional forces. Bonding can also be achieved by chemical reaction, i.e., formation of covalent bonds between binder and fibers.

As used herein "elastomer" refers to materials which exhibit both long-range deformability on application of stress and essentially complete recovery on removal Preferably, an elastomer of the present invention, at room temperature, can be stretched repeatedly to at least twice its original length and, after removal of the tensile load, will immediately and forcibly return to approximately its original length. Elastomers of the present invention are above the glass-transition temperature (Tg) and amorphous in the unstressed state to exhibit high local segmental mobility necessary for deformation. The chains are flexible and intermolecular (interchain) forces are weak. The elastomers of the present invention possess a sufficient number of chemical or physical cross-links to form a continuous network in order to restrain chain slippage.

Thermoplastic elastomers of the present invention have many of the properties of conventional elastomers such as vulcanized rubbers, but are processed as thermoplastics rather than thermosets. Transition from a fluid melt to a solid is reversible. Thermoplastic elastomers of the present invention are multiphase systems, where at least one phase is soft and rubbery and another hard. With thermoplastic elastomers, the transition from a processible melt to a solid, rubberlike object is rapid and reversible and takes place upon cooling. Preferably, PHAs of the present invention which are processed into an elastomer have sufficiently high branch content to enable them to act as thermoplastic elastomers, with the crystalline areas acting as the hard segment and the amorphous segments acting as the soft segment. Thermoplastic elastomers of the present invention can be processed on conventional plastics equipment, such as injection molders.

Important structural parameters for thermoplastic elastomers are the molecular weight, the nature of the soft and hard segments, and the ratio of soft to hard segments. The ratio of hard to soft segments effects the total modulus of the elastomer, increasing with the proportion of the hard segments. Elastomers of the present invention comprising a PHA of the present invention can also be used in blend formulations with other polymers (or copolymers), even non-elastomeric PHAs, to increase impact strength and toughness in stiffer materials.

As used herein "adhesive" means a material that joins two other materials, called adherends, together. In one embodiment of the present invention, the adhesive is applied as a liquid, preferably of a low viscosity. In the liquid form the adhesive wets the adherend surface and flows into the crevices in the adherend surfaces. The liquid form of the adhesive is obtained by heating to the point that flow occurs, dissolving or dispersing the material in a solvent, or starting with liquid monomers or oligomers that polymerize or react after application. The adhesive then undergoes a phase change to a solid either by cooling, solvent evaporation, or reaction, in order for the joint to acquire the necessary strength to resist shearing forces. However, pressure-sensitive adhesives are an exception, since no phase change occurs.

The PHAs of the present invention may be processed into a variety of adhesives, including but not limited to, hot melt, solution, dispersion and pressure sensitive adhesives. Adhesives comprising PHAs may be used, for example, to adhere seeds onto biodegradable tapes and to adhere together components used to form wreath rings.

As used herein, "hot-melt adhesive" refers to a thermoplastic polymer or copolymer that is heated to obtain a liquid of flowable viscosity, and, after application, cooled to obtain a solid. Generally, the molecular weight of the adhesive is tailored to provide flowability in the melt, but still be strong enough in the solid form to resist shearing forces experienced in the application. Due to their thermoplastic properties, the PHAs of the present invention are particularly useful as hot-melt adhesives. The primary feature of hot-melt adhesives is the ability of the thermoplastic material to flow above a certain temperature, high above the normal use temperature of the bond. Upon cooling, the material hardens, either through passing through the glass transition temperature of one of the components, or the crystallization temperature. This hardening lends physical integrity to the bond. In PHAs, the mode of solidification is crystallization.

The adhesives of the present invention may be applied either as solutions, in water or an organic solvent, or in the form of aqueous dispersions. In either form, the solvent must be removed after application for the adhesive to attain the required solid form. The solution or dispersion is usually applied to one of the surfaces to be bonded, and the solvent removed before the second surface is joined; often, heating is required to expedite the drying step. With porous substrates, such as paper or wood, final drying can take place after formation of the joint. Solids contents of the solutions vary from about 5% to about 95%, although values from about 20% to about 50% are most common.

As used herein, "dispersion" refers to when adhesives are prepared by true emulsion polymerization or dispersed as larger particles in some carrier fluid. In addition to their economic advantage, dispersions containing from about 40% to about 50% solids offer lower viscosity than solutions, even if the solids are high molecular-weight polymers. Adhesive dispersions of the present invention may be prepared by high shear in the presence of surfactants to obtain waterborne formulations, procedures which are well known to those skilled in the art.

Another type of adhesive of the present invention is a pressure-sensitive adhesive. Unlike other adhesives, the pressure-sensitive adhesives do not change their physical state from the initial application, to the final breaking of the adhesive bond. They remain permanently deformable, and may alter under even slight application of pressure. They are adhesives that in dry form are permanently tacky at room temperature and that firmly adhere to surfaces upon mere contact. The most common form of pressure-sensitive adhesive is on a backing, usually in tape form.

Coated articles, including encapsulated seeds and chemicals, may be formed using any conventional coating technique. Coating techniques include extrusion coating, roller coating, brush coating, dip coating, spray coating, electrostatic coating, centrifugal coating and cast coating. Articles may be coated with melted PHA, and then exposed to a coolant, such as water, by any acceptable method, such as dipping or spraying. As used herein, "coated items" includes items formed from laminates of a paper substrate and a film or sheet comprising a PHA.

Coating equipment may be used to apply a surface coating to a substrate. Suitable substrates include porous web, such as paper or cardboard. The coatings may serve as barriers, decorative coatings, or other purposes. Coating may be used to apply adhesive for laminating one web to another or for manufacturing of pressure-sensitive tapes and labels. It also may be used for saturation of a porous web, such as paper, in order to improve its resistance to moisture or grease penetration, or to improve its strength.

Coatings when applied must be sufficiently fluid to be spread into a uniformly thin layer across the web. Therefore, coatings are applied as solutions in organic solvents, as aqueous solutions or emulsions, as a hot melt (solid molten or softened by heat), or as a reactive liquid that solidifies by a polymerization reaction induced either thermally or by radiation. Extrusion coating is similar to hot-melt coating.

Coatings may be applied directly to the substrate, or may be cast to another surface, dried, and later transferred to the substrate. This transfer coating process is used for manufacturing of, for example, pressure-sensitive label stock: the adhesive is first applied to a silicone-coated release liner, dried, and then laminated to the label face stock. Coatings may be applied to the web material wound in rolls, or to precut sheets. Coated items may be formed by pressing coated paperboard blanks between forming dies.

In extrusion coating a film of molten polymer is deposited between two moving webs in a nip created by a rubber pressure roll and a chrome-plated steel chill roll. In this continuous operation, rolls of material are unwound, new rolls are automatically spliced on the fly, and the surface of the substrate is prepared by chemical priming or other surface treatment to make it receptive to the extrusion coating, and to help develop adhesion between the two materials.

Compositions for treating plaints or soil may comprise a PHA and a carrier, and, optionally an agricultural chemical. The compositions may be formed by preparing a PHA, grinding or milling the PHA to form small beads, and dispersing the beads into a carrier. Alternatively, the beads may be formed by encapsulating an agricultural chemical with PHA, and then dispersing the beads into a carrier.

Additional embodiments and modifications within the scope of the claimed invention will be apparent to one of ordinary skill in the art. Accordingly, the scope of the present invention shall be considered in terms of the following claims, and is understood not to be limited to the details of the methods or devises described in the specification.

What is claimed is:

1. An agricultural item comprising an anaerobically biodegradable polyhydroxyalkanoate copolymer comprising two randomly repeating monomer units wherein the first randomly repeating monomer unit has the structure:

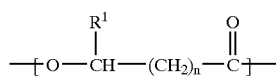

(i)

wherein R¹ is H or a $C_{1-2}$ alkyl, and n is 1; and
the second randomly repeating monomer unit has the structure:

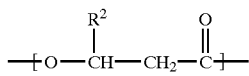

(ii)

wherein R² is a $C_{3-19}$ alkyl or a $C_{3-19}$ alkenyl;
wherein at least 50% of the randomly repeating monomer units have the structure of the first randomly repeating monomer unit; and wherein the agricultural item is selected from the group consisting of erosion control covers, nets, pots, wreath rings, mulches, plant stakes, labels, twines, ropes, seed-containing devices, chemical-containing devices, encapsulated seeds, encapsulated chemicals, plant coatings and mixtures thereof and wherein said anaerobically biodegradable polyhydroxyalkanoate copolymer is non-brittle and has a melting temperature from about 60 C to about 140 C.

2. An agricultural item according to claim 1, wherein the anaerobically biodegradable plastic further comprises a third randomly repeating monomer unit having the structure:

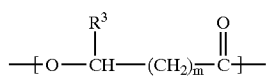

(iii)

wherein R³ is H, a $C_{1-19}$ alkyl or a $C_{1-19}$ alkenyl, and m is 1; and
wherein the additional randomly repeating monomer unit is not the same as the first randomly repeating monomer unit or the second randomly repeating monomer unit.

3. An agricultural item according to claim 1, wherein R¹ is a $C_{1-2}$ alkyl and n is 1.

4. An agricultural item according to claim 1, wherein R¹ is a $C_1$ alkyl.

5. An agricultural item according to claim 1, wherein R¹ is H and n is 2.

6. An agricultural item according to claim 1, where the item is substantially free of plasticizers.

7. An agricultural item according to claim 6, wherein the chemical is selected from fertilizers, pesticides, herbicides, compounds which are unpalatable to animals, compounds which are attractant to beneficial insects and mixtures thereof.

8. A method of treating a plant comprising the step of contacting at least a portion of a plant with a composition comprising an anaerobically biodegradable polyhydroxyalkanoate copolymer comprising two randomly repeating monomer units wherein the first randomly repeating monomer unit has the structure:

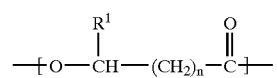

(i)

wherein R¹ is H or a $C_{1-2}$ alkyl, and n is 1; and
the second randomly repeating monomer unit has the structure:

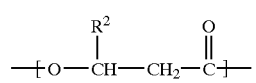

(ii)

wherein R² is a $C_{3-19}$ alkyl or a $C_{3-19}$ alkenyl;
wherein at least 50% of the randomly repeating monomer units have the structure of the first randomly repeating monomer unit and wherein said anaerobically biodegradable polyhydroxyalkanoate copolymer is non-brittle and has a melting temperature from about 60 C to about 140 C.

9. A method according to claim 8, wherein the anaerobically biodegradable plastic further comprises a third randomly repeating monomer unit having the structure:

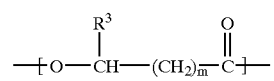

(iii)

wherein R³ is H, a $C_{1-19}$ alkyl or a $C_{1-19}$ alkenyl, and m is 1; and
wherein the additional randomly repeating monomer unit is not the same as the first randomly repeating monomer unit or the second randomly repeating monomer unit.

10. A method according to claim 8, wherein the plant is a cut flower.

11. A method according to claim 8, wherein the step of contacting the plants comprises contacting leaves with the composition, and wherein moisture loss by the leaves is decreased.

12. A method according to claim 8, wherein the plant is protected from a pest selected from plant pathogens, arachnids, insects, animals, weeds and mixtures thereof.

13. A method according to claim 8, wherein the composition further comprises an ingredient selected from the group consisting of pesticides, herbicides, fungicides, mildewcides and mixtures thereof.

14. A method according to claim 8, wherein the composition further comprises an ingredient unpalatable to animals.

15. A method for the controlled release of a chemical comprising treating the chemical with an anaerobically biodegradable polyhydroxyalkanoate copolymer comprising two randomly repeating monomer units wherein the first randomly repeating monomer unit has the structure:

(i)

wherein R¹ is H or a $C_{1-2}$ alkyl, and n is 1; and
the second randomly repeating monomer unit has the structure:

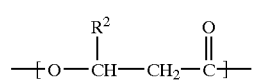

(ii)

wherein R² is a $C_{3-19}$ alkyl or a $C_{3-19}$ alkenyl; and
wherein at least 50% of the randomly repeating monomer units have the structure of the first randomly repeating monomer unit and wherein said anaerobically biodegradable polyhydroxyalkanoate copolymer is non-brittle and has a melting temperature from about 60 C to about 140 C.

16. A method according to claim 15, wherein the anaerobically biodegradable plastic further comprises a third randomly repeating monomer unit having the structure:

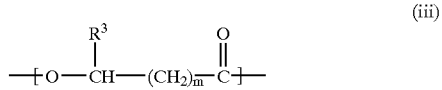

(iii)

wherein $R^3$ is H, a $C_{1-19}$ alkyl or a $C_{1-19}$ alkenyl, and m is 1; and wherein the additional randomly repeating monomer unit is not the same as the first randomly repeating monomer unit or the second randomly repeating monomer unit.

17. A method according to claim 15, wherein step of treating the chemical comprises coating the chemical with the biodegradable polyhydroxyalkanoate copolymer.

18. A method according to claim 15, wherein step of treating the chemical comprises incorporating the chemical into a device comprising the biodegradable polyhydroxyalkanoate copolymer.

19. A method according to claim 15, wherein $R^1$ is a $C_{1-2}$ alkyl and n is 1.

20. A method according to claim 18, wherein $R^1$ is a $C_1$ alkyl.

* * * * *